(12) United States Patent
Nakano et al.

(10) Patent No.: US 7,993,506 B2
(45) Date of Patent: Aug. 9, 2011

(54) GAS SENSOR

(75) Inventors: Yoshihiro Nakano, Komaki (JP);
Shinichi Nakagawa, Konan-ku (JP);
Yuichi Koyama, Niwa-gun (JP); Takio Kojima, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 204 days.

(21) Appl. No.: 12/015,238

(22) Filed: Jan. 16, 2008

(65) Prior Publication Data

US 2008/0257732 A1     Oct. 23, 2008

(30) Foreign Application Priority Data

Jan. 16, 2007   (JP) ................................ 2007-007194
Dec. 27, 2007   (JP) ................................ 2007-337393

(51) Int. Cl.
*G01N 27/26*      (2006.01)
*G01N 27/417*     (2006.01)
*B05D 5/12*       (2006.01)

(52) U.S. Cl. ............ 204/429; 73/23.2; 428/402; 501/38
(58) Field of Classification Search .................. 204/400, 204/421–429; 427/126.2, 201, 282, 376.2; 422/78; 73/31.06, 23.2; 205/781, 783.5–785, 205/787; 428/402; 501/38
See application file for complete search history.

(56) References Cited

U.S. PATENT DOCUMENTS

| | | | |
|---|---|---|---|
| 4,706,493 A * | 11/1987 | Chang et al. .................. 73/31.06 |
| 5,593,558 A | 1/1997 | Sugino et al. | |
| 5,766,434 A | 6/1998 | Fujii et al. | |
| 6,086,948 A * | 7/2000 | Roth et al. .................. 427/126.2 |
| 2006/0024202 A1 * | 2/2006 | Atsumi et al. .................. 422/78 |
| 2008/0242746 A1 * | 10/2008 | Morimura et al. .............. 516/90 |

FOREIGN PATENT DOCUMENTS

| | | |
|---|---|---|
| EP | 0 372 425 A2 | 6/1990 |
| EP | 1 568 991 A1 | 8/2005 |
| JP | 61-075249 A | 4/1986 |
| JP | 03-293552 A | 12/1991 |
| JP | 04-269650 A | 9/1992 |
| JP | 4-343060 A | 11/1992 |
| JP | 05-126777 A | 5/1993 |
| JP | 05-069667 U | 9/1993 |
| JP | 06-174683 A | 6/1994 |
| JP | 7-260729 | * 10/1995 |
| JP | 9-166567 A | 6/1997 |
| JP | 11-183420 A | 7/1999 |
| JP | 3171745 A | 3/2001 |
| JP | 2002-328109 A | 11/2002 |
| JP | 2004-184219 A2 | 7/2004 |
| JP | 2005-315874 A | 11/2005 |

OTHER PUBLICATIONS

"Test Methods for Pore Size Distribution of Fine Ceramic Green Body by Mercury Porosimetry", Japanese Industrial Standard, JIS R 1655 (JFCA/JSA), May 20, 2003, 19 Pages, (With English Abstract).

* cited by examiner

*Primary Examiner* — Alexa D Neckel
*Assistant Examiner* — Jennifer Dieterle
(74) *Attorney, Agent, or Firm* — Sughrue Mion, PLLC

(57) ABSTRACT

There is provided a gas sensor, including a gas sensing film formed of an oxide semiconductor material and a gas-permeable protection layer formed of oxide particles and arranged on the gas sensing film. The oxide particles of the protection layer have an average particle size of 500 nm or smaller.

10 Claims, 15 Drawing Sheets

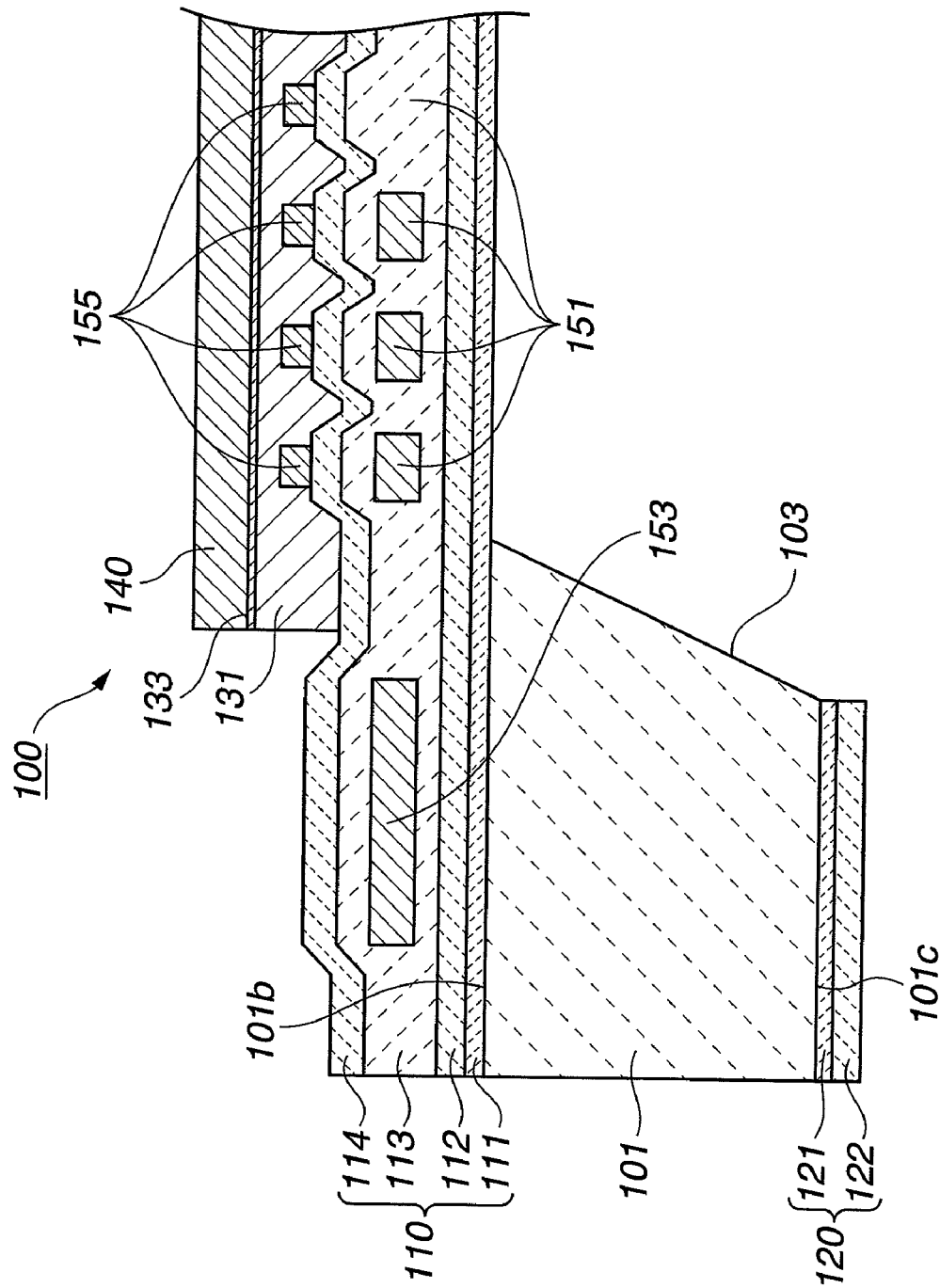

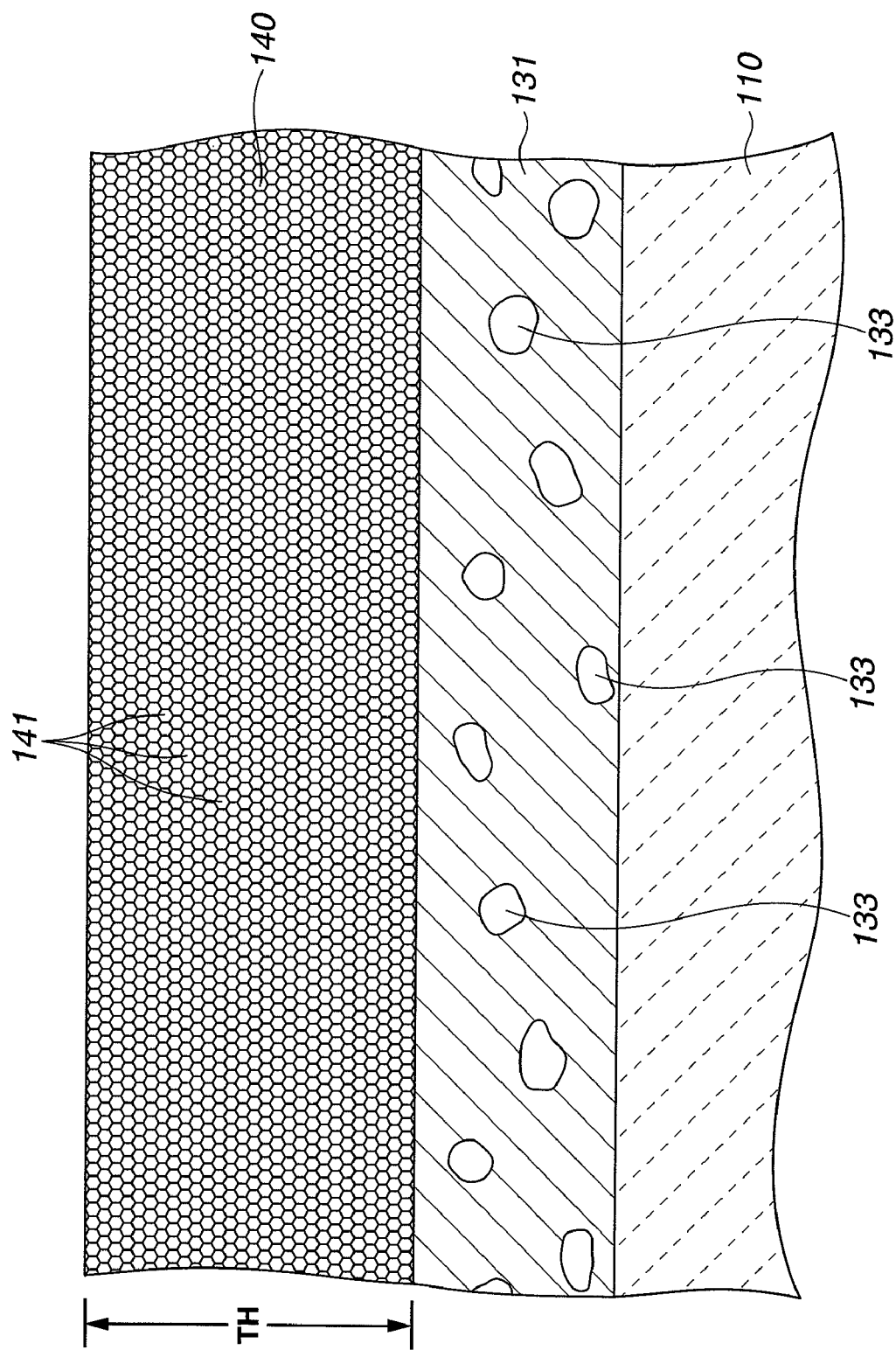

GAS SENSOR

BACKGROUND OF THE INVENTION

The present invention relates to a gas sensor having a gas sensing film formed of an oxide semiconductor material and covered by a gas-permeable protection layer.

Various types of gas sensors have been proposed, one of which is a so-called oxide semiconductor gas sensor that has a gas sensing film formed of an oxide semiconductor material such as tin oxide so as to change its electrical properties in response to concentration variations in measurement gas and thereby detect the presence (or absence) or concentration of the measurement gas. The oxide semiconductor gas sensor deteriorates in performance over time and lack performance stability when the gas sensing film is poisoned by silicon etc.

There are some conceivable ways to prevent the oxide semiconductor gas sensor from performance deterioration due to poisoning of the gas sensing film. One way is to pretreat the gas sensing film with some poisoning material such as silicon and change the sensor performance to some extent in advance of actual sensor use. It is however difficult to regulate the degree of such sensor prepoisoning treatment in a variety of sensor use environments and, even by sensor prepoisoning treatment, merely possible to prevent a large change in the sensor performance at the early stage of poisoning during actual sensor use. Another way is to apply a gas-permeable protection layer onto the gas sensing film and protect the gas sensing film from any poisoning material. Japanese Laid-Open Patent Publication No. 9-166567 (abbreviated as "JP9-166567A") proposes one such type of gas sensor having a gas sensing film formed of tin oxide and a filter layer (protection layer) formed of a mixture of tin oxide and amorphous alumina so as to obtain improvements in poisoning resistance and secular performance stability and reduction in initial stabilization time. Japanese Patent No. 3171745 (abbreviated as "JP3171745B") proposes another gas sensor having a gas sensing film formed of tin oxide and a coating layer (protection layer) formed of tungstic oxide, titanium oxide or zinc oxide etc. so as to show high sensitivity to odorous gas and low sensitivity to non-odorous gas and obtain S/N ratio improvement for accurate odor detection in a lower concentration range.

SUMMARY OF THE INVENTION

Each of JP9-166567A and JP3171745B gives a technical idea of selecting the material of the protection layer as appropriate in order to improve the poisoning resistance and performance stability of the oxide semiconductor gas sensor. However, the oxide semiconductor gas sensor cannot attain sufficient poisoning resistance and fails to prevent deterioration in performance during long-time use only by selecting the material of the protection layer as appropriate.

It is therefore an object of the present invention to provide an oxide semiconductor gas sensor capable of attaining sufficiently high poisoning resistance and securing stable gas detection performance over long-time use.

According to an aspect of the present invention, there is provided a gas sensor, comprising: a gas sensing film formed of an oxide semiconductor material; and a gas-permeable protection layer formed of oxide particles and arranged on the gas sensing film, wherein the oxide particles of the protection layer have an average particle size of 500 nm or smaller.

The other objects and features of the present invention will also become understood from the following description.

BRIEF DESCRIPTION OF THE DRAWINGS

FIGS. 2 and 3 are section views of the gas sensor when taken along line A-A and line B-B of FIG. 1, respectively.

FIG. 17 is a schematic view of a gas sensor according to another exemplary embodiment of the present invention.

DESCRIPTION OF THE EMBODIMENTS

The present invention will be described below with reference to the drawings.

The following embodiment of the present invention refers to a gas sensor 100 for detecting the presence (or absence) or concentration of a measurement gas. Upon appropriate selection of sensor component materials, the gas sensor 100 can be designed to show sensitivity to various kinds of gases such as a reducing gas e.g. carbon monoxide gas, hydrocarbon gas (liquefied petroleum gas (LPG), town gas, natural gas, methane gas, halogenated hydrocarbon gas etc.), alcohol gas, aldehyde gas or hydrogen gas, an oxidizing gas e.g. nitrogen dioxide gas, a strong odor gas e.g. ammonia gas, hydrogen sulfide gas or ethyl acetate gas or the like. By way of example, the gas sensor 100 is designed as an oxidizing gas sensor, and more specifically a nitrogen dioxide sensor, in the present embodiment.

Figure 1A:
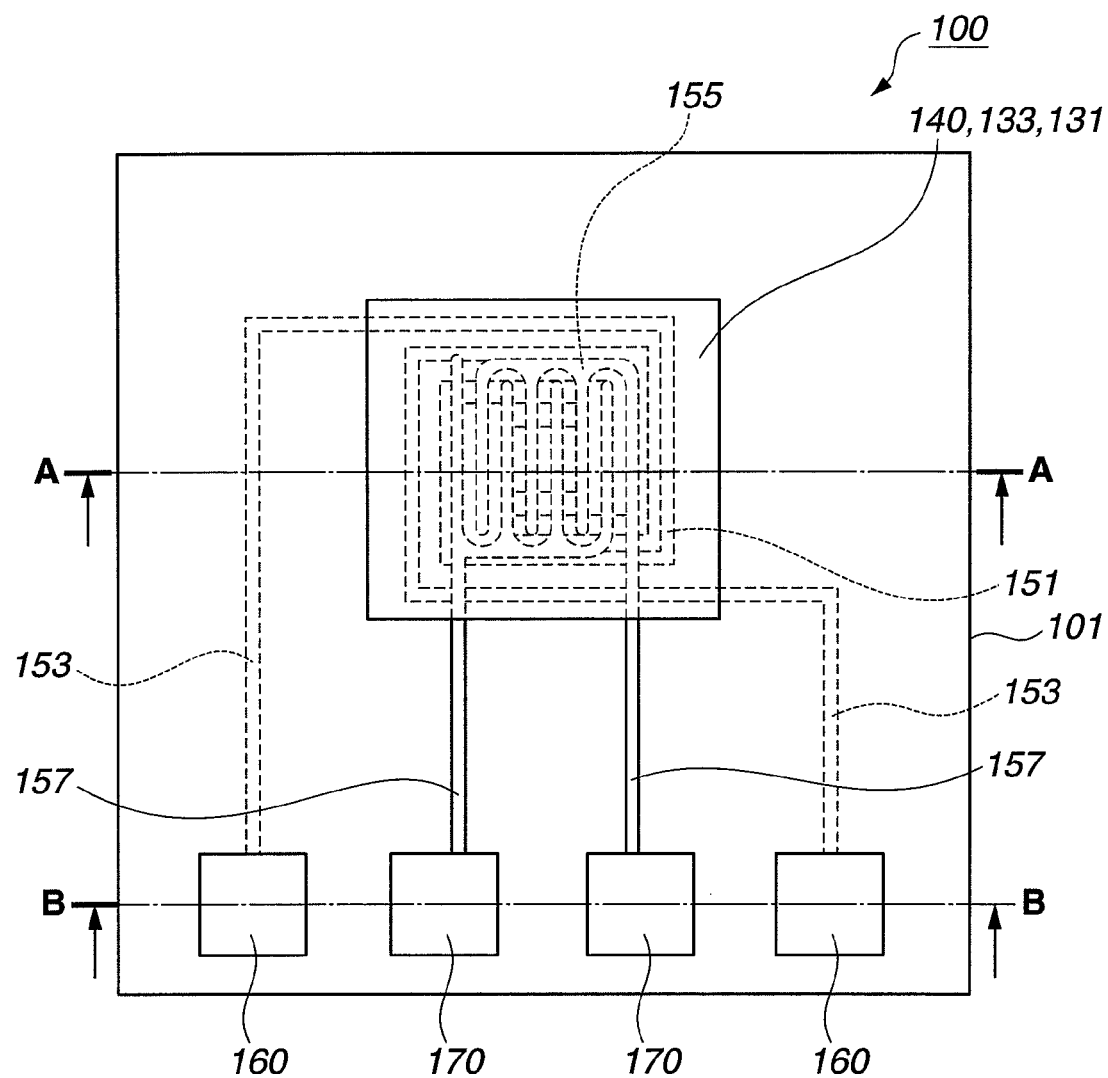
FIGS. 1A and 1B is a top view and a side view of a gas sensor according to one exemplary embodiment of the present invention.
Figure 1B:
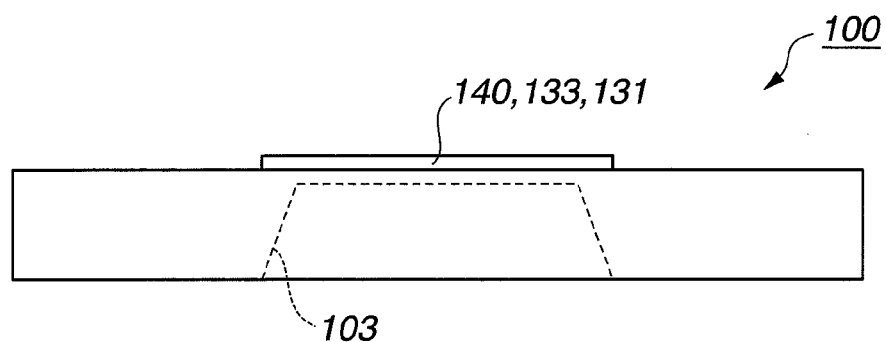

Referring to FIGS. 1A, 1B and 2, the gas sensor 100 has a rectangular plan form provided with a substrate 101, a pair of insulating films 110 and 120, a gas sensing film 131, a plurality of catalyst particles 133 and a gas-permeable protection layer 140.

There is no particular restriction on the substrate 101. The substrate 101 can be formed of any appropriate substrate material such as silicon or alumina. In the present embodiment, the substrate 101 is formed of silicon with a thickness of 400 μm.

Figure 3:
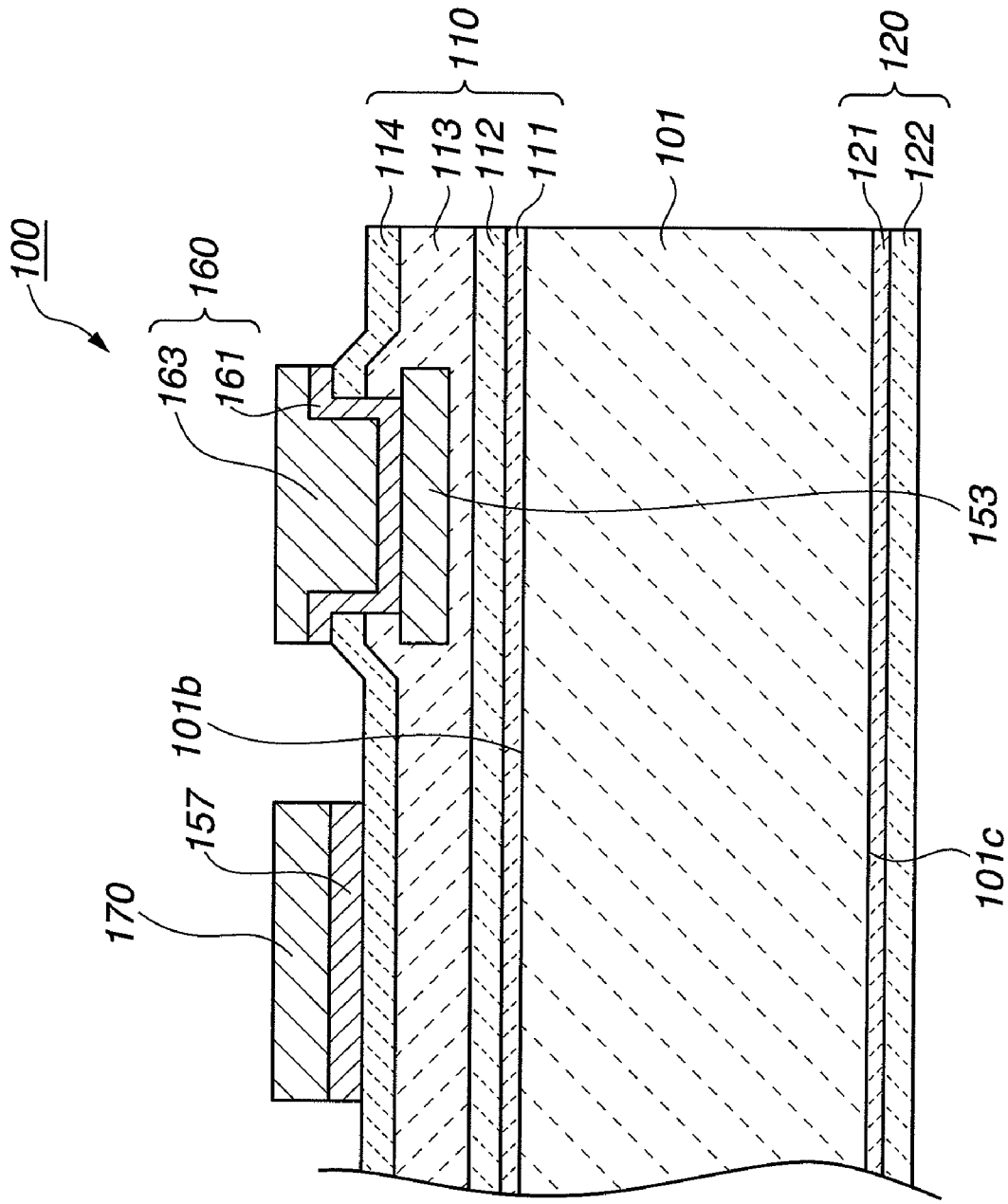

There are also no particular restrictions on the insulating films 110 and 120. In the present embodiment, the insulating film 110 has four insulating layers: a first insulating layer 111 formed of silicon oxide with a thickness of 100 nm, a second insulating layer 112 formed of silicon nitride with a thickness of 200 nm, a third insulating layer 113 formed of silicon oxide with a thickness of 200 nm and a fourth insulating layer 114 formed of silicon nitride with a thickness of 200 nm as shown in FIGS. 2 and 3. Although not illustrated in FIG. 4 for the sake of simplicity, these insulating layers 111, 112, 113 and 114 are laminated in order of mention on a first surface 101$b$ of the substrate 101. The insulating film 120 has two insulating layers: a first insulating layer 121 formed of silicon oxide with a thickness of 100 nm and a second insulating layer 122 formed of silicon nitride with a thickness of 100 nm as shown in FIGS. 2 and 3 in the present embodiment. These insulating layers 121 and 122 are laminated in order of mention on a second surface 101$c$ of the substrate 101.

The gas sensing film 131 is arranged on the fourth insulating layer 114 of the insulating film 110 and formed of an oxide semiconductor material so as to change its electrical properties (electrical resistance) in response to the existence of the measurement gas for detection of gas concentration variations (gas contamination). There is no particular restriction on the structure of the gas sensing film 131. The gas sensing film 131 may be formed by either thin-film forming process or thick-film forming process. In the present embodiment, the gas sensing film 131 is formed of tin oxide with a thickness of 200 nm.

Figure 4:
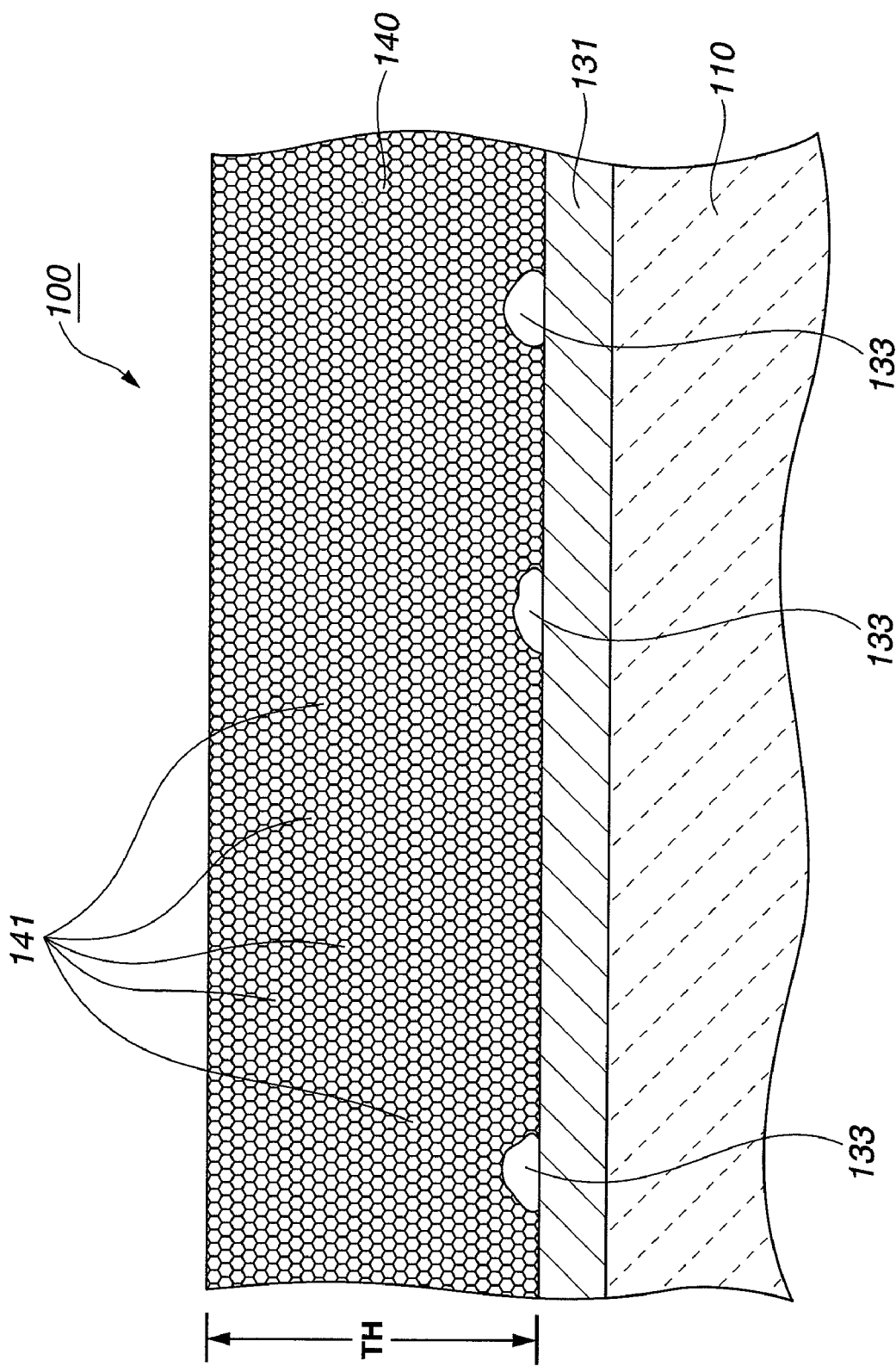
FIG. 4 is an enlarged schematic section view of gas sensing part of the gas sensor of FIG. 1.

There is no particular restriction on the catalyst particles 133 as long as the catalyst particles 133 undergo a proper catalytic reaction of the measurement gas. Any appropriate catalytically active material is used for the catalyst particles 133. For example, the catalyst particles 133 can be formed of palladium when the gas sensor 100 is a reducing gas sensor. When the gas sensor 100 is an oxidizing gas sensor, the catalyst particles 133 can alternatively be formed of gold. The catalyst particles 133 are scattered over the gas sensing film 131 and covered by the protection layer 140 as shown in FIG. 4, or dispersed in the gas sensing film 131 as shown in FIG. 17. In order to lead the measurement gas through the protection layer 140, bring the measurement gas into contact with both of the gas sensing film 131 and the catalyst particles 133 efficiently and thereby impart higher gas sensitivity to the gas sensor 100, the catalyst particles 133 are preferably scattered over the gas sensing film 131 and covered by the protection layer 140. In the present embodiment, the catalyst particles 133 are formed of gold so that the electrical resistance of the tin oxide gas sensing film 131 changes in response to variations in oxidizing gas concentration (nitrogen dioxide concentration) under the action of the catalyst particles 133. Further, the catalyst particles 133 are scattered over the gas sensing film 131 and covered by the protection layer 140 as shown in FIG. 4 in the present embodiment although illustrated in the form of a layer in FIG. 2 for the sake of simplicity.

The protection layer 140 has a porous structure formed of oxide particles 141. The oxide particles 141 have an average particle size of 500 nm or smaller and are closely packed to show gas permeability in a thickness direction of the protection layer 140. By controlling the average particle size of the oxide particles 141 to within such a specific range, the protection layer 140 is able to trap any poisoning material such as silicon in the measurement gas efficiently and protect the gas sensing film 131 from the poisoning material without interfering the permeation of the measurement gas through the gas sensing film 131. It is thus possible to provide the gas sensor 100 with higher resistance against the poisoning material and reduce or prevent secular performance deterioration in the gas sensor 100.

In order for the protection layer 140 to attain a large specific surface area and thereby trap the poisoning material more efficiently, the average particle size of the oxide particles 141 is preferably 150 nm or smaller, more preferably 100 nm or smaller. The average particle size of the oxide particles 141 is also preferably 5 nm or greater in view of the fact that too small a particle size may cause too low a gas flow rate and result in sensor response deterioration.

Herein, the average particle size of the oxide particles 141 can be determined by performing focused ion beam (FIB) processing on the protection layer 140 with e.g. a FIB device "FB-2100" available from Hitachi Ltd. and observing a field of at least 30 oxide particles 141 of the protection layer 140 with e.g. a transmission electron microscope (TEM) "HD-2000" available from HITACHI Ltd.

There is no particular restriction on the structure of the protection layer 140 as long as the average particle size of the oxide particles 141 is in the range of 500 nm or smaller. The protection layer 140 may have a single-layer structure or a multi-layer structure. The oxide particles 141 may be of the same kind or different kinds. In the case where the oxide particles 141 of the protection layer 140 are of different kinds, these different kinds of oxide particles 141 may be mixed together uniformly or distributed at different locations (such as at upper and lower sides of the protection layer 140). The oxide particles 141 may be of different average particle sizes.

Any particles other than the oxide particles 141, e.g., the catalyst particles 133 may be included in the protection layer 140. However, if the catalyst particles 133 are totally incorporated in the protection layer 140 and are not in contact with the gas sensing film 131, the catalyst particles 133 undergo a catalytic reaction of the measurement gas within the protection layer 140 but not on the gas sensing film 131 so that the gas sensor 100 decreases in gas sensitivity. It is thus preferable that the catalyst particles 133 are not totally incorporated in the protection layer 140 and are kept in contact with the gas sensing film 131.

The oxide particles 141 can be any of metal or non-metal oxide particles such as titanium oxide particles, tungstic oxide particles, alumina particles, silica particles or tin oxide particles. It is preferable that the oxide particles 141 are metal oxide particles, particularly titanium oxide particles. The ability of the titanium oxide particles to trap the poisoning material such as silicon is higher than those of the other oxide particles. The use of such titanium oxide particles as the oxide particles 141 of the protection layer 140 thus allows the gas sensor 100 to attain higher poisoning resistance and reduce or prevent secular performance deterioration more effectively.

It is also preferable that the protection layer 140 satisfies the dimensional relationship of $20 \leq TH/D \leq 500$ where D is the average particle size (nm) of the oxide particles 141 and TH is the thickness (nm) of the protection layer 140. Herein, the thickness TH of the protection layer 140 means a vertical dimension from the interface between the gas sensing film 131 and the protection layer 140 to the upper, exposed surface of the protection layer 140. When $TH/D \geq 20$, the protection layer 140 produces a greater effect of trapping the poisoning material so as to protect the gas sensing film 131 from the poisoning material more effectively. If $TH/D > 500$, however, the gas permeability of the protection layer 140 may be impaired. When $TH/D \leq 500$ is satisfied, the protection layer 140 secures sufficient gas permeability. It is thus possible to obtain further improvements in the poisoning resistance and secular performance stability of the gas sensor 100 upon satisfaction of the relationship of $20 \leqq TH/D \leqq 500$. It is more preferable to satisfy the relationship of $TH/D \leqq 300$ for higher sensor response.

Further, the volume of pores in the protection layer 140 with a pore size (diameter) smaller than or equal to the average particle size of the oxide particles 141 in the protection layer 140 preferably constitutes 50% or more of the total pore volume of the protection layer 140. In the presence of such a high percentage of small-sized pores in the protection layer 140, the oxide particles 141 are closely packed so that the protection layer 140 produces a greater poisoning material trap effect to protect the gas sensing film 131 from the poisoning material while securing sufficient gas permeability without interfering with the permeation of the measurement gas through to the gas sensing film 131. The gas sensor 100 is thus able to attain higher poisoning resistance and reduce or prevent secular performance deterioration more effectively.

The pore size distribution of the protection layer 140 can be measured by mercury porosimetry (according to JIS R 1655) or nitrogen gas adsorption method. In the mercury porosimetry, the pore size distribution can be measured with e.g. an automated mercury porosimeter "Autopore IV 9510" available from Shimadzu Corporation by the application of a mercury pressure 0.5 to 36000 psia. In the nitrogen gas adsorption method, the pore size distribution can be measured by analyzing a nitrogen adsorptive curve with e.g. a high-end, full-automatic gas adsorption instrument available from BEL Japan Inc. The mercury porosimetry is more suitable for large pore size measurements, whereas the nitrogen gas adsorption method is more suitable for small pore size measurements. The pore size distribution measurement method may be thus selected as appropriate between the mercury porosimetry and the nitrogen gas adsorption method so as to e.g. carry out pore size measurements by the mercury porosimetry in a pore size range of 100 nm or greater and by the nitrogen gas adsorption method in a pore size range of smaller than 100 nm.

It is preferable that the volume of pores in the protection layer 140 with a pore size (diameter) greater than or equal to 3 times the average particle size of the oxide particles 141 constitutes 10% or less (including 0%) of the total pore volume of the protection layer 140. More specifically, it is preferable that the volume of pores in the protection layer 140 with a pore size (diameter) of 200 nm or greater as measured by the mercury porosimetry constitutes 5% or less (including 0%) of the total pore volume of the protection layer 140. In the presence of such a low percentage of large-sized pores in the protection layer 140, the oxide particles 141 are closely packed so that the protection layer 140 produces a greater poisoning material trap effect to protect the gas sensing film 131 from the poisoning material while securing sufficient gas permeability without interfering with the permeation of the measurement gas through to the gas sensing film 131. The gas sensor 100 is thus able to attain higher poisoning resistance and reduce or prevent secular performance deterioration more effectively.

Furthermore, it is preferable that, when observed with a scanning electron microscope (SEM), there are no pores opening at the surface of the protection layer 140 with a pore opening size (diameter) greater than or equal to 10 times the average particle size of the oxide particles 141. In the presence of no observable, largely-opened pores in the surface of the protection layer 140, the oxide particles 141 are closely packed so that the protection layer 140 produces a greater poisoning material trap effect to protect the gas sensing film 131 from the poisoning material while securing sufficient gas permeability without interfering with the permeation of the measurement gas through to the gas sensing film 131. The gas sensor 100 is thus able to attain higher poisoning resistance and reduce or prevent secular performance deterioration more effectively.

The protection layer 140 is preferably formed by depositing or applying the oxide particles 141 onto the gas sensing film 131 and heat treating the oxide particles 141 at such a temperature as not to cause sintering of the oxide particles 141. With such a heat treatment, the oxide particles 141 are closely packed by favorable physical bonding so that the protection layer 140 produces a greater poisoning material trap effect to protect the gas sensing film 131 from the poisoning material while securing sufficient gas permeability without interfering with the permeation of the measurement gas through to the gas sensing film 131. The gas sensor 100 is thus able to attain higher poisoning resistance and reduce or prevent secular performance deterioration more effectively.

It is further preferable that the protection layer 140 has such a thickness that the catalyst particles 133 are unexposed to the outside through the protection layer 140 in order to increase the poisoning material trap effect of the protection layer 140 and protect the gas sensing film 131 from the poisoning material more effectively for improvements in poisoning resistance and secular performance stability.

In the present embodiment, the protection layer 140 is formed of titanium oxide particles 141 with an average particle size D of 20 nm and a layer thickness TH of 1000 nm so as to take on the thickness-to-average particle size ratio of $TH/D=50$, i.e., satisfy the relationship of $20 \leqq TH/D \leqq 500$ without the catalyst particles 133 being exposed to the outside through the protection layer 140. Further, the volume of pores in the protection layer 140 with a pore size smaller than or equal to 20 nm (the average particle size D of the oxide particles 141) constitutes about 88% of the total pore volume of the protection layer 140. The volume of pores in the protection layer 140 with a pore size greater than or equal to 60 nm (3 times or greater than the average particle size D of the oxide particles 141) constitutes about 1% of the total volume of the protection layer 140. The protection layer 140 has almost no pores with a pore size of 200 nm or greater as measured by the mercury poresimetry. There are no pores opening at the surface of the protection layer 140 with a pore opening size of 200 nm (10 times or greater than the average particle size D of the oxide particles 141) when the surface of the protection layer 140 is observed by SEM in the present embodiment. By the average particle size and pore size control of the protection layer 140, the gas sensor 100 becomes able to attain sufficiently high poisoning resistance and reduce or prevent secular performance deterioration more effectively as discussed above.

Referring to FIGS. 1A, 2 and 3, the gas sensor 100 also includes a heating resistor 151 embedded in the insulating layer 113, a pair of leads 153 embedded in the insulating layer 113 and electrically connected with the heating resistor 151 and contacts 160 arranged on the respective ends of the leads 153 to connect the leads 153 with an external circuit. The heating resistor 151 is energized by the external circuit through the leads 153 and the contacts 160 so as to heat the gas sensing film 131 to 200° C. or higher for activation of the gas sensing film 131. In the present embodiment, each of the heating resistor 151 and the leads 153 has a double-layer structure that consists of a tantalum layer with a thickness of 20 nm and a platinum layer with a thickness of 220 nm. Each of the contacts 160 is rectangular in planform and provided with a lead electrode 161 and a contact pad 163. The lead electrode 161 has a double-layer structure that consists of a titanium layer with a thickness of 20 nm and a platinum layer with a thickness of 40 nm. Further, the contact pad 163 is formed of gold with a thickness of 400 nm.

As shown in FIG. 2, the substrate 101 and the insulating film 120 are partially cut away to define a recess 103 at a position corresponding to the heating resistor 151 in such a manner that the insulating layer 111 becomes exposed at the bottom of the recess 103.

Referring again to FIGS. 1A, 2 and 3, the gas sensor 100 further includes an electrode 155 arranged on the insulating layer 114 at a position corresponding to the heating resistor 151 and covered by the gas sensing film 131, a pair of leads 157 arranged on the insulating layer 114 and electrically connected with the electrode 155 and contact pads 170 arranged on the leads 157 to connect the leads 157 with the external circuit so that the electrode 155 is energized by the external circuit through the leads 157 and the contact pads 170. In the present embodiment, each of the electrode 155 and the leads 157 has a double-layer structure that consists of a titanium layer with a thickness of 20 nm and a platinum layer with a thickness of 40 nm as is the case with the lead electrode 161. The contact pads 170 are rectangular in planform in the present embodiment. Further, the contact pads 170 are formed of gold as is the case with the contact pads 163 in the present embodiment.

The above-structured gas sensor 100 can be produced by the following procedure.

The silicon substrate 101 is first prepared, cleaned by immersing in a cleaner, and then, subjected to thermal oxidization in a heat treatment furnace to form the silicon oxide insulating layers 111 and 121 over the opposite first and second surfaces 101b and 101c of the substrate 101.

The silicon nitride insulating layers 112 and 122 are next formed on the insulating layers 111 and 121, respectively, by low-pressure chemical vapor deposition (LP-CVD) using $SiH_2Cl_2$ and $NH_3$ as a source gas.

A lower half part of the silicon oxide insulating layer 113 is formed on the insulating layer 112 by plasma CVD using tetraethoxysilane (TEOS) and $O_2$ as a source gas.

The tantalum layer and the platinum layer are formed successively by means of a direct current (DC) sputtering device on the lower part of the silicon oxide insulating layer 113. The resulting tantalum-platinum layer laminate is subjected to photolithographic resist patterning and wet etching so as to remove the unnecessary portion of the tantalum-platinum layer laminate and thereby produce the heating resistor 151 in a specific pattern together with the leads 153.

An upper half part of the silicon oxide insulating layer 113 is further formed on the lower part of the silicon oxide insulating layer 113 by plasma CVD using TEOS and $O_2$ as a source gas, whereby the insulating layer 113 becomes completed with the heating resistor 151 and the leads 153 being embedded in the insulating layer 113.

The silicon nitride insulating layer 114 is then formed on the insulating layer 113 by LP-CVD using $SiH_2Cl_2$ and $NH_3$ as a source gas.

After that, holes in which to form the contacts 160 are made through the insulating layers 113 and 114 by photolithographic resist patterning and dry etching so that some parts of the leads 153 are exposed through the respective contact holes.

The titanium layer and the platinum layers are formed successively by means of a DC sputtering device on the insulating layer 114 and in the contact holes in the insulating layers 113 and 114. The resulting titanium-platinum layer laminate is subjected to photolithographic resist patterning and wet etching so as to remove the unnecessary portion of the titanium-platinum layer laminate and thereby produce the electrode 155 in a specific pattern together with the leads 157 on the insulating layer 114 and the lead electrodes 161 in the contact holes. Further, the gold layer is formed by means of a DC sputtering device and subjected to photolithographic resist patterning and wet etching so as to produce the contact pads 163 on the lead electrodes 161 and the contact pads 170 on the leads 157.

A part of the insulating film 120 (the insulating layers 121 and 122) corresponding in position to the heating resistor 151 is subjected to photolithographic resist patterning, dry etching and anisotropic etching with a tetramethyl ammonium hydroxide (TMAH) solution, thereby defining the recess 103 so that the insulating layer 111 becomes exposed to the outside at the bottom of the recess 103.

The tin oxide gas sensing film 131 is formed on the insulating layer 114 by thin-film forming process with a radio frequency (RF) sputtering device so as to cover the electrode 155 by the gas sensing film 131. For example, the RF sputtering conditions can be set to a sputtering gas of argon and oxygen with a gas content ratio Ar/(Ar+O) of 28%, a sputtering gas pressure of 2.0 Pa, a power density of 4.34 $kW/cm^2$, a film forming speed of 4.8 nm/min, a substrate temperature of 240° C., a sputtering time of 42 minutes and a target area of 5×10 inch (12.7×25.4 cm).

The gold catalyst particles 133 are formed on the gas sensing film 131 by means of a DC sputtering device without heating the substrate. For example, the DC sputtering conditions can be set to a sputtering gas of argon, a sputtering gas pressure of 2.0 Pa, a power density of 0.62 $kW/cm^2$, a film forming speed of 11.4 nm/min, a sputtering time of 48 seconds and a target area of 5×10 inch (12.7×25.4 cm). The catalyst particles 133 are subsequently heat treated by means of a RF sputtering device or a vacuum heat treatment furnace for 3 hours at 360° C. in an atmosphere with an oxygen concentration of 10 ppm or lower, preferably 0.2 to 5 ppm.

The forming processes of the gas sensing film 131 and the catalyst particles 133 are not limited to the above. In the case where the catalyst particles 133 are dispersed in the gas sensing film 131 as shown in FIG. 17, the gas sensing film 131 can be formed by e.g. preparing a paste of tin oxide particles 141, catalyst particles 133, binder and viscosity improver as appropriate, applying the paste to the insulating layer 114 by thick-film printing, and sintering the paste After that, the protection layer 140 is formed on the gas sensing film 131 and the catalyst particles 133 as follows. Maskings are applied to the contacts 160 and the contact pads 170. On the other hand, an oxide powder of desired particle size and polyacrylic ammonium are dispersed in water to prepare an oxide particle sol of given viscosity e.g. 50 mPa·s. The sol is spin coated on the masked gas sensing film 131 and catalyst particles 133 under the given conditions. The thickness of the protection layer 140 can be adjusting by controlling the spin coat conditions. For example, the spin coat conditions are set to a spin speed of 5000 rpm, a substrate temperature of 25° C. and a relative ambient humidity of 40% RH. The resulting sol coating is allowed to air-dry and heated for 1 hour at such a temperature as not cause sintering of the oxide particles 141 e.g. at 350° C. in a heat treatment furnace so as to complete the protection layer 140 with the oxide particles 141 being physically bonded and closely packed together. Alternatively, the protection layer 140 may be formed by dipping the sol onto the gas sensing film 131 and drying and heat treating the resulting sol coating.

Finally, the gas sensor 100 is completed by cutting out the substrate 101 to a planar size of 2.6×2 mm with e.g. a dicing saw.

As described above, the oxide particles 141 of the protection layer 140 are closely packed on the gas sensing film 131 so as to trap the poisoning material effectively and protect the gas sensing film 131 from the poisoning material without interfering with the permeation of the measurement gas through to the gas sensing film 131 by controlling the average particle size of the oxide particles 141 to 500 nm or smaller. It is therefore possible for the gas sensor 100 to secure higher poisoning resistance and prevent secular sensor performance deterioration during use.

The present invention will be described in more detail by reference to the following examples. It should be however noted that the following examples are only illustrative and not intended to limit the invention thereto.

Evaluations of Sensor Poisoning Resistance and Performance Stability

EXAMPLES 1-4

Test samples of the gas sensor 100 were produced by the above procedure such that the oxide particles 141 of the protection layer 140 were titanium oxide particles with an average particle size of D=7 nm in Example 1, D=20 nm in Example 2 and D=100 nm in Example 3 and tungstic oxide particles with an average particle size of D=300 nm in Example 4. The average particle size D of the oxide particles 141 was determined by performing FIB process on the protection layer 140 and observing the protection layer 140 with TEM "HD-2000" available from HITACHI Ltd.

Durability tests were carried out on the gas sensors 100 of Examples 1 to 4 in order to determine the sensitivity of the gas sensor 100 to nitrogen oxide gas ($NO_2$) in the presence of silicon as a poisoning material before the initiation of sensor energization and after 100, 200 and 400 hours of sensor energization. In the durability test, the gas sensor 100 was electrically connected with a measurement jig via gold wiring, placed in a measurement gas atmosphere, and then, energized to heat the heating resistor 151 to 250° C. and continuously apply a gas detection voltage to the gas sensing film 131. A mixed gas of nitrogen and 20.9 vol % oxygen with a relative humidity of 40% RH was used as a base gas of the measurement gas atmosphere and controlled to 25° C. As the poisoning material, 3 ppm of hexamethyldisilazane (organic silicon) was added to the base gas. The electrical resistance Ra of the gas sensor 100 (the gas sensing film 131) was measured in the measurement gas atmosphere. After a lapse of 5 seconds from the addition of 1 ppm of nitrogen dioxide gas (oxidizing gas) to the base gas, the electrical resistance Rg of the gas sensor 100 (the gas sensing film 131) was measured. The gas sensitivity of the gas sensor 100 was then determined as Rg/Ra. The threshold value of the gas sensitivity Rg/Ra for proper nitrogen oxide gas detection was 1.1. The test results are indicated in TABLE 1 and FIG. 5.

COMPARATIVE EXAMPLES 1-4

Test samples of gas sensors were produced in the same way as in Examples 1 to 4 except that the gas sensor had a protection layer formed of aluminum oxide particles with an average particle size of D=700 nm in Comparative Example 1; the gas sensor had a protection layer formed of titanium oxide particles with an average particle size of D=1000 nm in Comparative Example 2; the gas sensor had a protection layer formed of silicon oxide particles with an average particle size of 3000 nm; and the gas sensor had no protection layer in Comparative Example 4.

The gas sensors of Comparative Examples 1 to 4 were tested for the sensitivity to nitrogen oxide gas in the presence of silicon in the same way as to Examples 1 to 4. The test results are also indicated in TABLE 1 and FIG. 5.

TABLE 1

|  | Gas Sensitivity (Rg/Ra) Time (hr) | | | |
|---|---|---|---|---|
|  | 0 | 100 | 200 | 400 |
| Example 1 | 3.86 | 3.73 | 3.64 | 3.57 |
| Example 2 | 3.13 | 4.59 | 3.94 | 4.09 |
| Example 3 | 2.83 | 3.45 | 2.88 | 2.82 |
| Example 4 | 1.91 | 2.08 | 2.07 | 2.07 |
| Comparative Example 1 | 1.69 | 1.43 | 1.34 | 1.23 |
| Comparative Example 2 | 2.12 | 1.59 | 1.45 | 1.20 |
| Comparative Example 3 | 1.69 | 1.50 | 1.28 | 1.15 |
| Comparative Example 4 | 3.60 | 1.64 | 1.41 | 1.12 |

Figure 5:
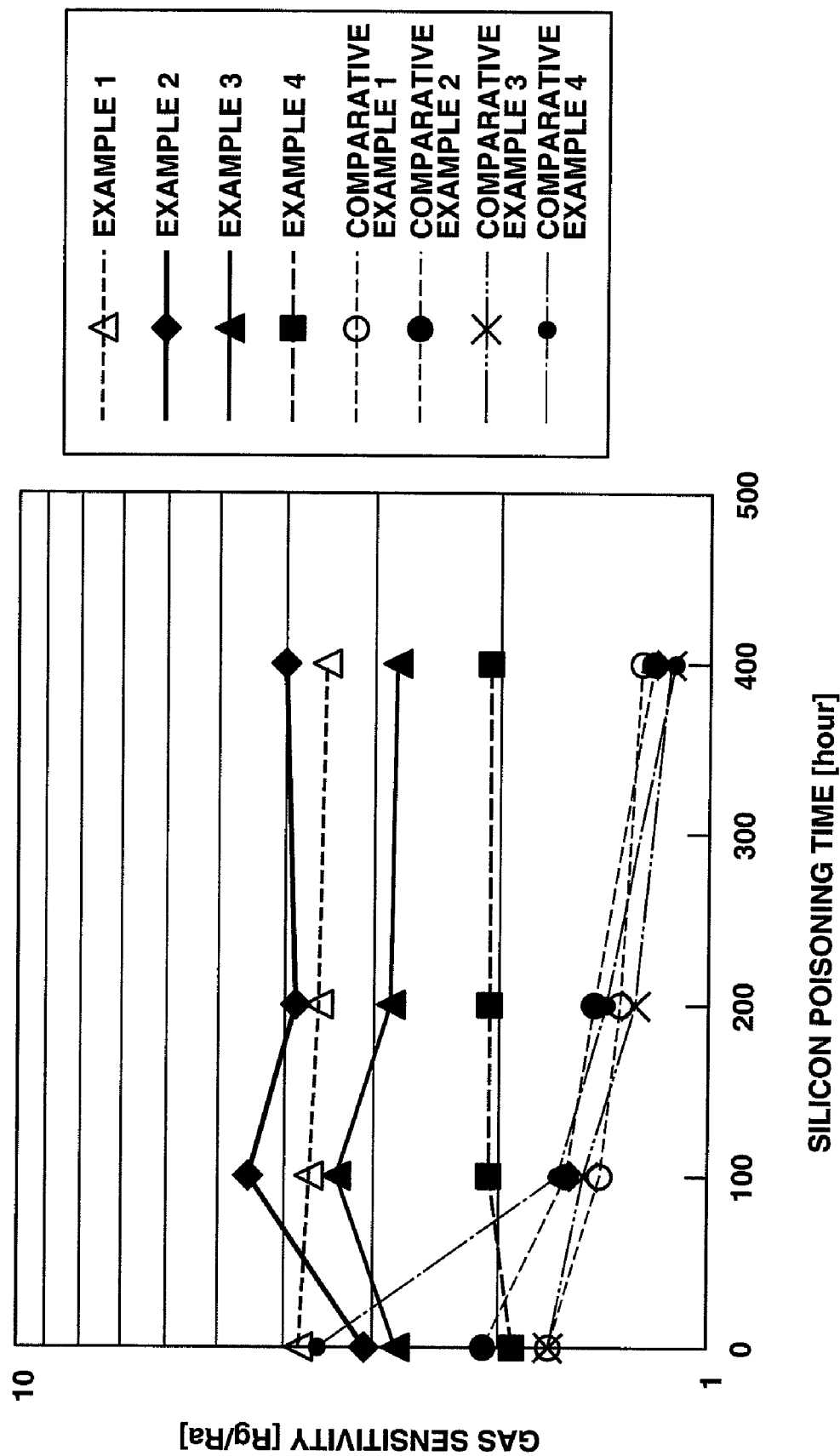
FIG. 5 is a graph showing the test results on gas sensitivity Rg/Ra in Examples 1 to 4 and in Comparative Examples 1 to 4.

As is seen from TABLE 1 and FIG. 5, the gas sensitivity Rg/Ra was sufficiently higher than the threshold value (Rg/Ra ≧1.1) throughout 400 hours of sensor energization in Examples 1 to 4. Namely, the gas sensors 100 of Examples 1 of 4 had sufficiently high gas sensitivity Rg/Ra even after 400 hours of sensor energization. On the other hand, the gas sensitivity Rg/Ra was gradually decreased to about the threshold value during 400 hours of sensor energization in Comparative Examples 1 to 4.

The change rate Sc of the gas sensitivity Rg/Ra was also calculated by the following equation: Sc=log B/log A where A is the gas sensitivity before the initiation of the durability test; and B is the gas sensitivity after a lapse of time from the initiation of the durability test. The threshold value of the gas sensitivity change rate Sc for proper performance stability was 0.5. The calculation results are indicated in TABLE 2 and FIG. 6.

TABLE 2

|  | Gas Sensitivity Change Rate (Sc) Time (hr) | | | |
|---|---|---|---|---|
|  | 0 | 100 | 200 | 400 |
| Example 1 | 1.00 | 0.97 | 0.96 | 0.94 |
| Example 2 | 1.00 | 1.34 | 1.20 | 1.23 |
| Example 3 | 1.00 | 1.19 | 1.02 | 1.00 |
| Example 4 | 1.00 | 1.13 | 1.13 | 1.13 |
| Comparative Example 1 | 1.00 | 0.68 | 0.56 | 0.40 |
| Comparative Example 2 | 1.00 | 0.62 | 0.50 | 0.24 |
| Comparative Example 3 | 1.00 | 0.78 | 0.47 | 0.27 |
| Comparative Example 4 | 1.00 | 0.39 | 0.27 | 0.09 |

Figure 6:
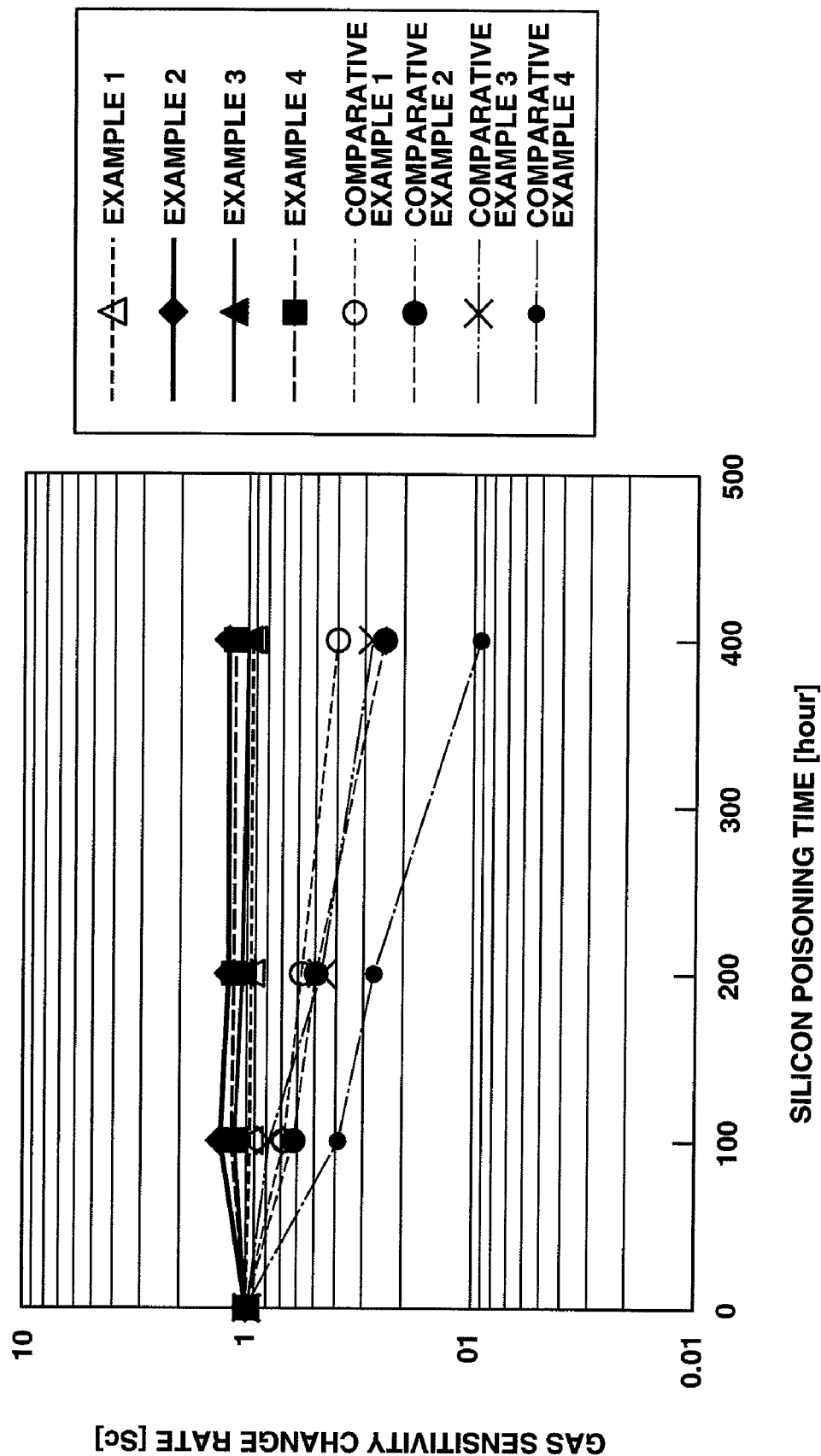
FIG. 6 is a graph showing the test results on gas sensitivity change rate Sc in Examples 1 to 4 and in Comparative Examples 1 to 4.

As is seen from TABLE 2 and FIG. 6, the gas sensitivity change rate Sc was sufficiently higher than the threshold value (Sc ≧0.5) throughout 400 hours of sensor energization in Examples 1 to 4. The gas sensors 100 of Examples 1 to 4 had sufficiently high gas sensitivity Rg/Ra even after 400 hours of sensor energization. On the other hand, the gas sensitivity change rate Sc became lower than the threshold value so that the gas sensitivity Rg/Ra was significantly lowered during 400 hours of sensor energization in Comparative Examples 1 to 4.

It has been shown that the gas sensor 100 can attain improved resistance to poisoning by silicon (organic silicon) and prevent secular performance deterioration by the formation of the protection layer 140 using the oxide particles 141 of small average particle size D≦500 nm.

EXAMPLES 5-7 AND COMPARATIVE EXAMPLES 5-6

Test samples of the gas sensor 100 were produced in the same way as in Examples 1 to 4 except that the titanium oxide particles 141 of the protection layer 140 had the same average particle size of D=20 nm but different thickness-to-average particle size ratio of TH/D=25 in Example 5, TH/D=50 in Example 6 and TH/D=100 in Example 7. Further, test samples of gas sensors were produced in the same way as in Examples 5 to 7 except that the gas sensor had a protection layer formed of titanium oxide particles with a thickness-to-average particle size ratio of TH/D=15 in Comparative Example 5; and the gas sensor had no protection layer in Comparative Example 6 as in the case of Comparative Example 4. The gas sensors 100 of Examples 5 to 7 and the gas sensors of Comparative Examples 5 and 6 were tested for the sensitivity to nitrogen oxide gas ($NO_2$) in the presence of silicon as a poisoning material in the same way as of Examples 1 to 4 and Comparative Examples 1 to 4. The test results are indicated in TABLE 3 and FIG. 7.

TABLE 3

| | Gas Sensitivity (Rg/Ra) Time (hr) | | | |
|---|---|---|---|---|
| | 0 | 100 | 200 | 400 |
| Example 5 | 2.35 | 2.30 | 1.86 | 1.79 |
| Example 6 | 2.52 | 2.92 | 3.53 | 2.68 |
| Example 7 | 1.61 | 1.51 | 1.59 | 1.83 |
| Comparative Example 5 | 1.69 | 1.43 | 1.34 | 1.23 |
| Comparative Example 6 | 3.60 | 1.64 | 1.41 | 1.12 |

Figure 7:
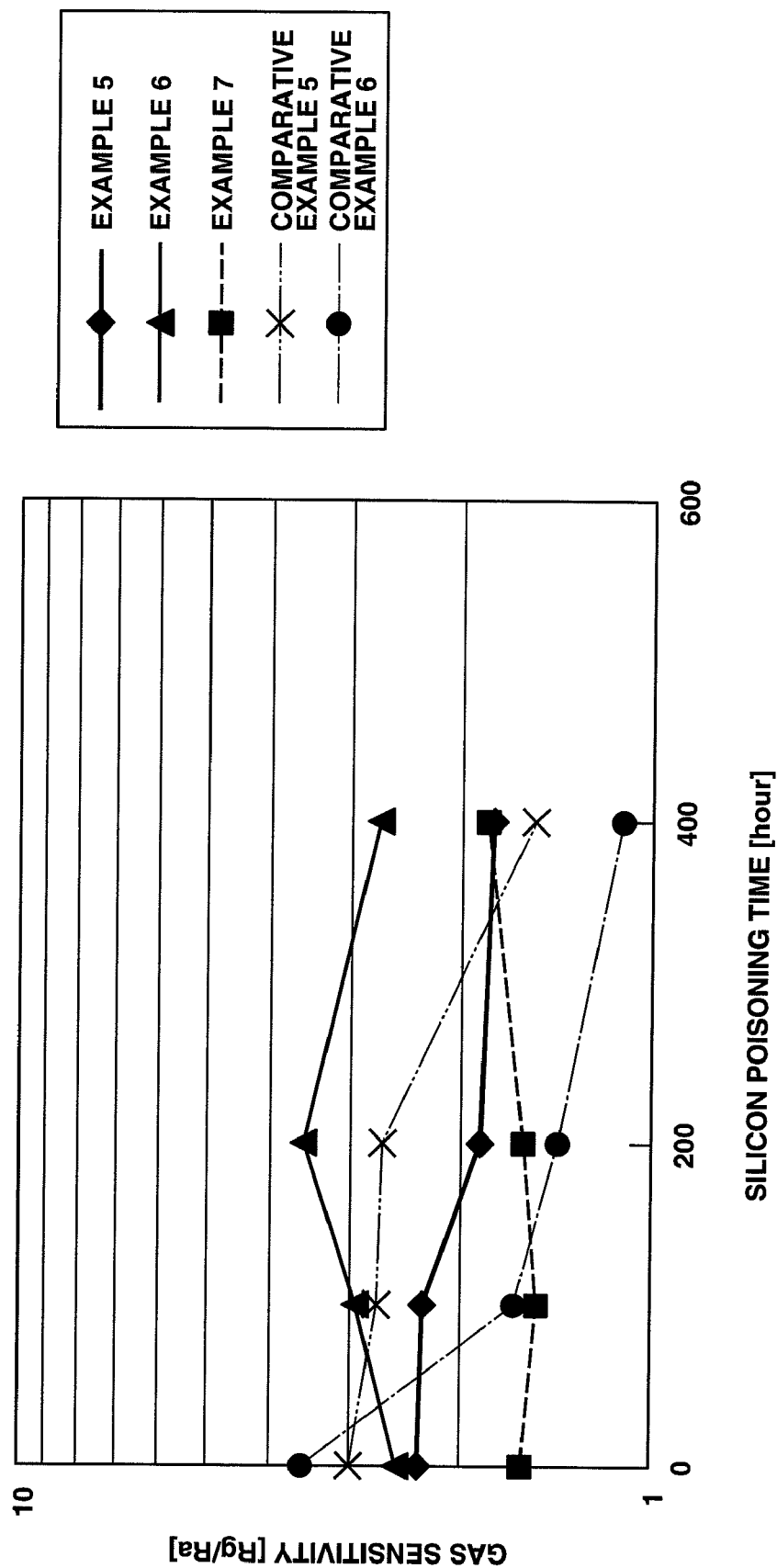
FIG. 7 is a graph showing the test results on gas sensitivity Rg/Ra in Examples 5 to 7 and in Comparative Examples 5 and 6.

As is seen from TABLE 3 and FIG. 7, the gas sensitivity Rg/Ra was sufficiently higher than the threshold value (Rg/Ra $\geq$ 1.1) throughout 400 hours of sensor energization in Examples 5 to 7. Namely, the gas sensors 100 of Examples 5 to 7 had sufficiently high gas sensitivity Rg/Ra even after 400 hours of sensor energization. On the other hand, the gas sensitivity Rg/Ra was gradually decreased to about the threshold value during 400 hours of sensor energization in Comparative Examples 5 and 6.

The gas sensitivity change rate Sc was also calculated in the same way as above. The calculation results are indicated in TABLE 4 and FIG. 8.

TABLE 4

| | Gas Sensitivity Change Rate (Sc) Time (hr) | | | |
|---|---|---|---|---|
| | 0 | 100 | 200 | 400 |
| Example 5 | 1.00 | 0.98 | 0.73 | 0.68 |
| Example 6 | 1.00 | 1.16 | 1.37 | 1.07 |
| Example 7 | 1.00 | 0.87 | 0.97 | 1.27 |
| Comparative Example 5 | 1.00 | 0.91 | 0.90 | 0.39 |
| Comparative Example 6 | 1.00 | 0.39 | 0.27 | 0.09 |

Figure 8:
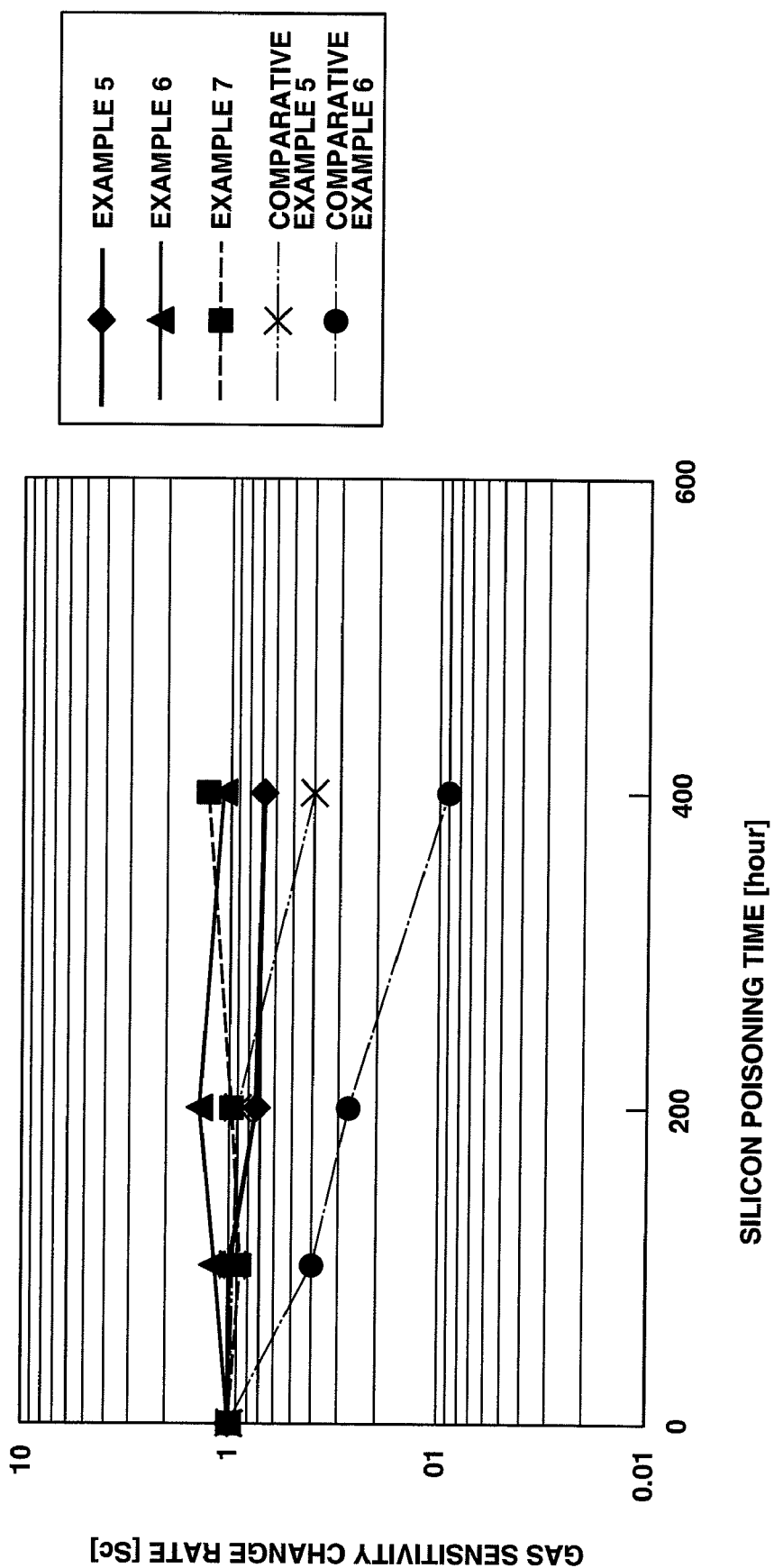
FIG. 8 is a graph showing the test results on gas sensitivity change rate Sc in Examples 5 to 7 and in Comparative Examples 5 and 6.

As is seen from TABLE 4 and FIG. 8, the gas sensitivity change rate Sc was sufficiently higher than the threshold value (Sc $\geq$ 0.5) throughout 400 hours of sensor energization in Examples 5 to 7. The gas sensors 100 of Examples 5 to 7 had sufficiently high gas sensitivity Rg/Ra even after 400 hours of sensor energization. On the other hand, the gas sensitivity change rate Sc became lower than the threshold value so that the gas sensitivity Rg/Ra was significantly lowered during 400 hours of sensor energization in Comparative Examples 5 and 6.

It has been shown that the gas sensor 100 can attain improved resistance to poisoning by silicon (organic silicon) and prevent secular performance deterioration upon satisfaction of the dimensional relationship of TH/D$\geq$20.

EXAMPLE 8

A test sample of the gas sensor 100 was produced in the same way as in Examples 1 to 4 except that the titanium oxide particles 141 of the protection layer 140 had an average particle size of D=150 nm in Example 8. The gas sensor 100 of Example 8 was tested for the sensitivity to nitrogen oxide gas ($NO_2$) in the presence of silicon as a poisoning material in the same way as above. The test results are indicated in TABLE 5 and FIG. 9.

TABLE 5

| | Gas Sensitivity (Rg/Ra) Time (hr) | | | |
|---|---|---|---|---|
| | 0 | 100 | 200 | 400 |
| Example 8 | 2.51 | 3.08 | 2.41 | 2.41 |

Figure 9:
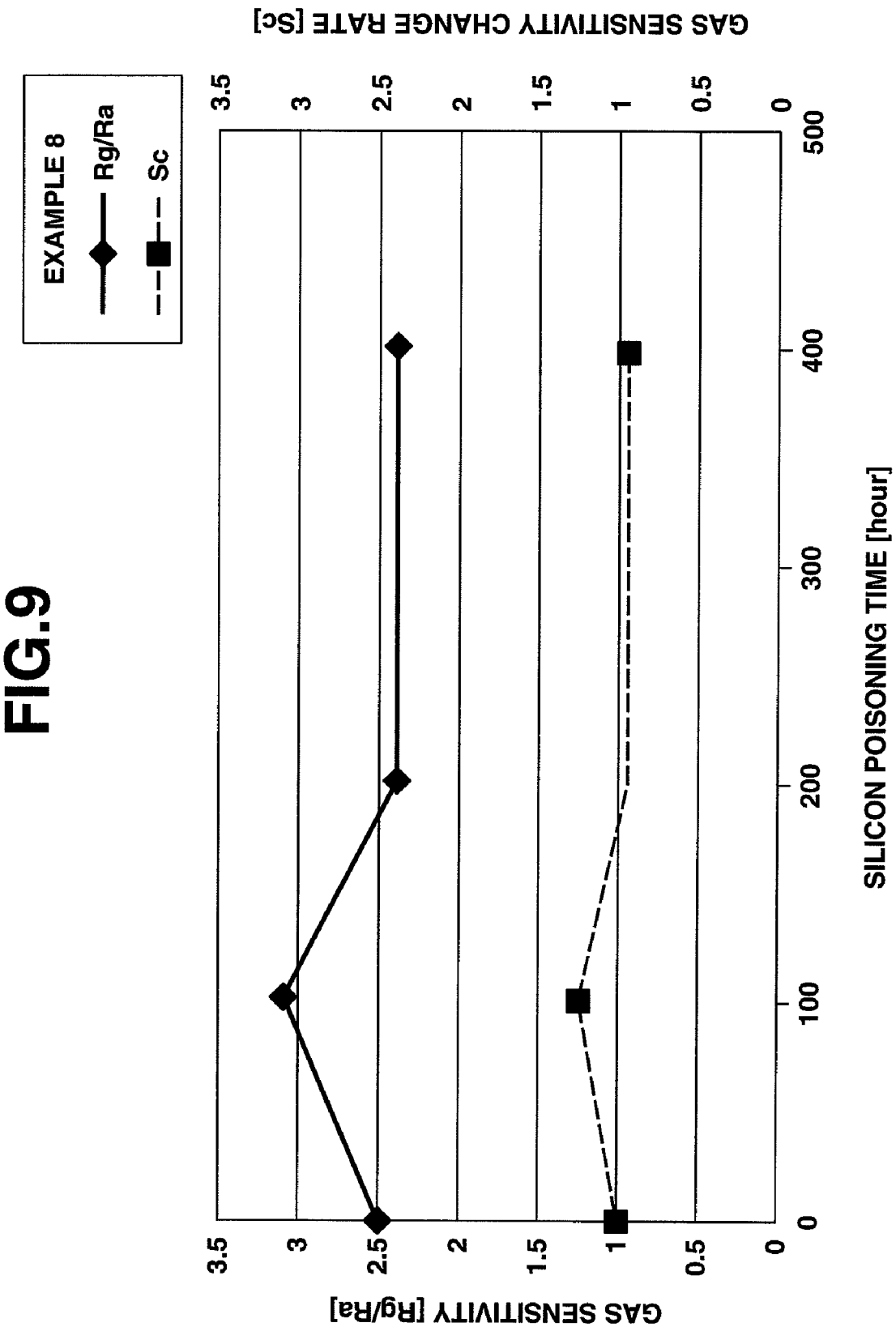
FIG. 9 is a graph showing the test results on gas sensitivity Rg/Ra and gas sensitivity change rate Sc in Example 8.

As is seen from TABLE 5 and FIG. 9, the gas sensitivity Rg/Ra was sufficiently higher than the threshold value (Rg/Ra $\geq$ 1.1) throughout 400 hours of sensor energization in Example 8. Namely, the gas sensor 100 of Example 8 had sufficiently high gas sensitivity Rg/Ra even after 400 hours of sensor energization.

The gas sensitivity change rate Sc was also calculated in the same way as above. The calculation results are indicated in TABLE 6 and FIG. 9.

TABLE 6

| | Gas Sensitivity Change Rate (Sc) Time (hr) | | | |
|---|---|---|---|---|
| | 0 | 100 | 200 | 400 |
| Example 8 | 1.00 | 1.22 | 0.96 | 0.96 |

As is seen from TABLE 6 and FIG. 9, the gas sensitivity change rate Sc was sufficiently higher than the threshold value (Sc $\geq$ 0.5) throughout 400 hours of sensor energization in Example 8. The gas sensor 100 of Example 8 had sufficiently high gas sensitivity Rg/Ra even after 400 hours of sensor energization.

It has been shown that the gas sensor 100 can attain improved resistance to poisoning by silicon (organic silicon) and prevent secular performance deterioration by the formation of the protection layer 140 using the oxide particles 141 of smaller average particle size D$\leq$150 nm.

Evaluations of Protection Layer Porosity

The gas sensors 100 of Examples 1, 2, 4 and 8 were first tested for the pore size distribution of the protection layer 140 as follows.

Porous bulks of titanium oxide particles and tungstic oxide particles were produced by the same film forming and heat treatment processes as in Examples 1, 2, 4 and 8. More specifically, the oxide particles and polyacrylic ammonium (as a dispersant) were dispersed in water, thereby yielding an oxide particle sol with a viscosity of 50 mPa·s. The sol was spin coated on a substrate with a given thickness. The resulting sol coating was allowed to air-dry and heated in a heat treatment furnace for 1 hour at 350° C. so as not to cause sintering of the oxide particles. By this, the porous bulk was completed with the oxide particles closely packed together by physical bonding. The porous bulk had an average particle size of D=7 nm, 20 nm, 300 nm, 150 nm, a diameter of 10 mm and a thickness of 15 mm as a test sample corresponding the protection layer 140 of Examples 1, 2, 4, 8. (Hereinafter, the porous bulks corresponding to the protection layers 140 of Examples 1, 2, 4 and 8 are just referred to as the bulks of Examples 1, 2, 4 and 8.)

Figure 10:
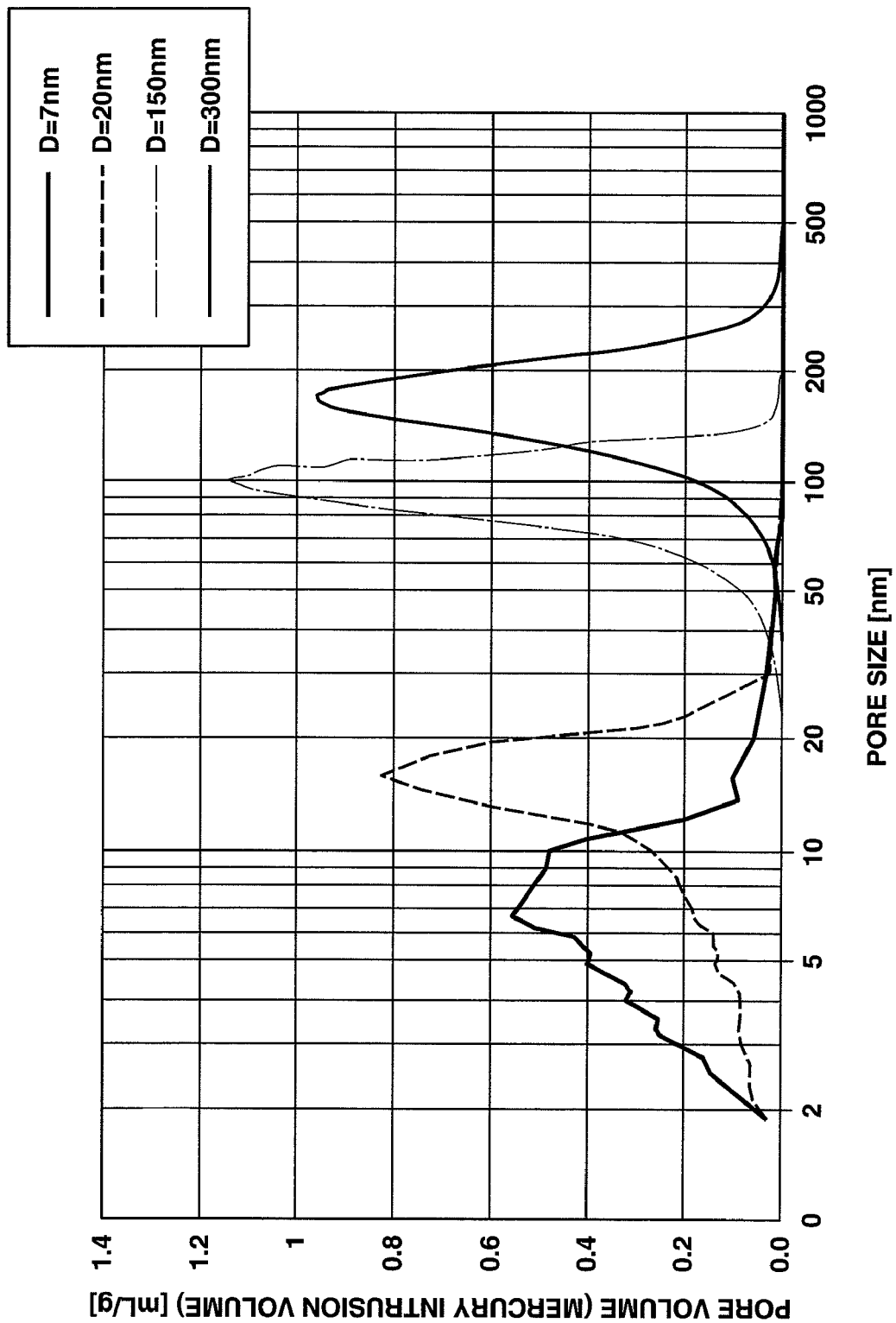
FIGS. 10 and 11 are graphs showing the test results on protection layer porosity in Examples 1, 2, 4 and 8.
Figure 11:
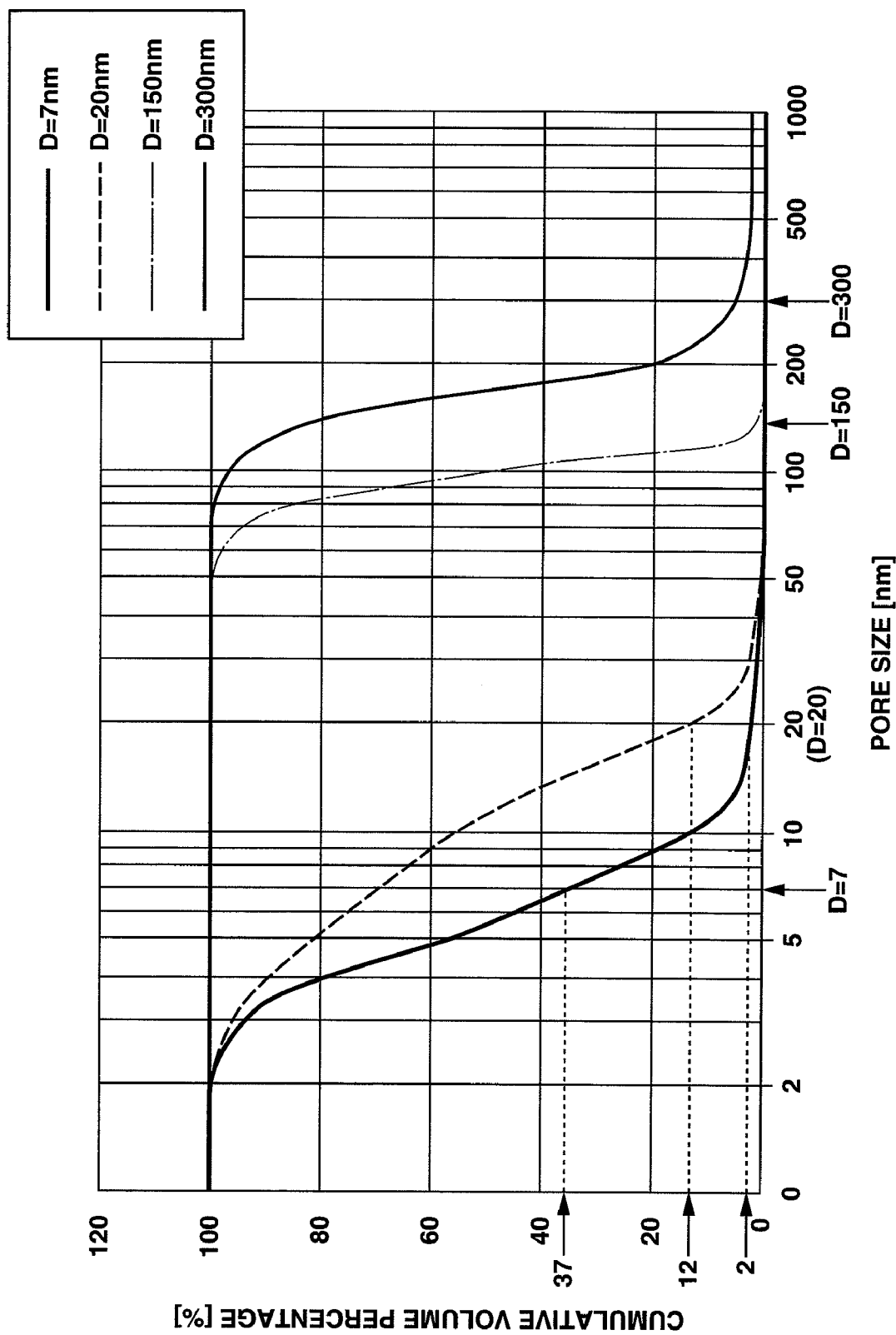

Pore size measurements were made on the bulks of Examples 1 and 2 by mercury porosimetry according to JIS R 1655 in a pore size range of 100 nm or greater and by nitrogen gas adsorption method in a pore size range of smaller than 100 nm. On the other hand, pore size measurements were made on the bulks of Examples 4 and 8 only by mercury porosimetry according to JIS R 1655. In the mercury porosimetry, the pore size distribution was measured with an automated mercury porosimeter "Autopore IV 9510" available from Shimadzu Corporation by the application of a mercury pressure 0.5 to 36000 psia. In the nitrogen gas adsorption method, the pore size distribution was measured by analyzing a nitrogen adsorptive curve with a high-end, full-automatic gas adsorption instrument available from BEL Japan Inc. The pore size distribution was also indicated in terms of the cumulative pore volume percentages by integration of the measurement results. The measurement/calculation results are indicated in FIGS. 10 and 11.

In the case of the bulk of Example 1 (average particle size: D=7 nm), the volume percentage of pores in the bulk with a pore size greater than 7 nm was 37%. In other words, the volume percentage of pores in the bulk of Example 1 with a pore size smaller than or equal to 7 nm was 63%, i.e., 50% or more based on the total bulk pore volume. Further, the volume percentage of pores in the bulk of Example 1 with a pore size greater than or equal to 21 nm (3 times the average particle size D) was 2%, i.e., 10% or less based on the total bulk pore volume. There were no pores (0%) in the bulk of Example 1 with a pore size of 200 nm or greater as measured by the mercury porosimetry.

Similarly, in the case of the bulk of Example 2 (average particle size: D=20 nm), the volume percentage of pores in the bulk with a pore size smaller than or equal to 20 nm was 88%, i.e., 50% or more based on the total bulk pore volume. Further, the volume percentage of pores in the bulk of Example 2 with a pore size greater than or equal to 60 nm (3 times the average particle size D) was 1%, i.e., 10% or less based on the total bulk pore volume. There were no pores (0%) in the bulk of Example 2 with a pore size of 200 nm or greater as measured by the mercury porosimetry.

In the case of the bulk of Example 4 (average particle size: D=300 nm), the volume percentage of pores in the bulk with a pore size smaller than or equal to 300 nm was 96%, i.e., 50% or more based on the total bulk pore volume. Further, the volume percentage of pores in the bulk of Example 3 with a pore size greater than or equal to 900 nm (3 times the average particle size D) was 3%, i.e., 10% or less based on the total bulk pore volume.

In the case of the bulk of Example 8 (average particle size: D=150 nm), the volume percentage of pores in the bulk with a pore size smaller than or equal to 150 nm was 99%, i.e., 50% or more based on the total bulk pore volume. There were no pores (0%) with a pore size greater than or equal to 450 nm (3 times the average particle size D) and no pores (0%) with a pore size of 200 nm or greater as measured by the mercury porosimetry.

Furthermore, the surface of the protection layer 140 was observed by SEM in Examples 2, 4 and 8.

Figure 12:
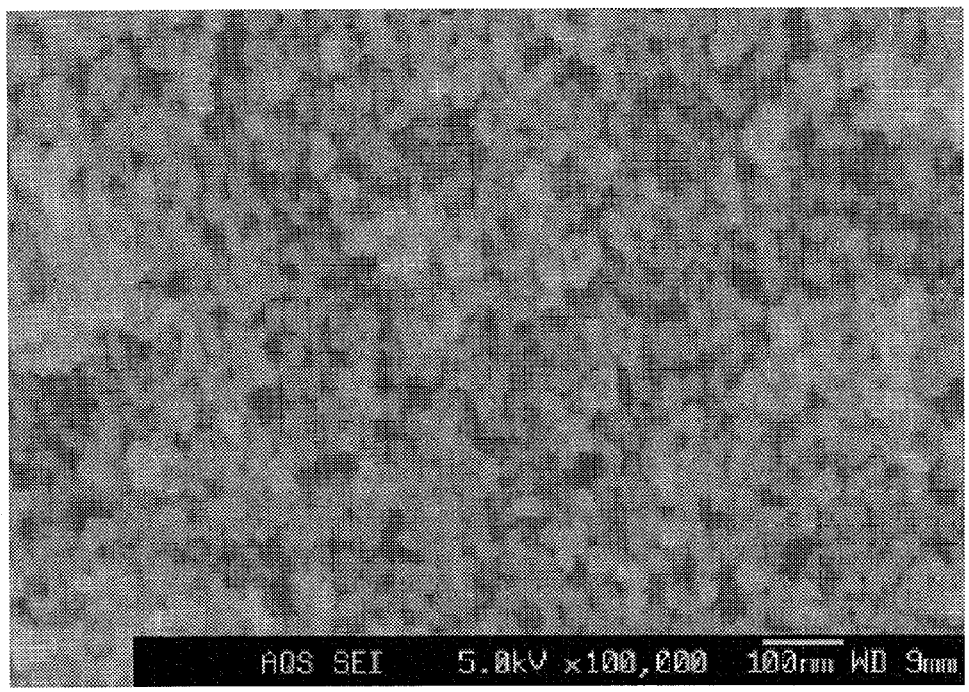
FIG. 12 is a SEM image of protection layer surface in Example 2.
Figure 13:
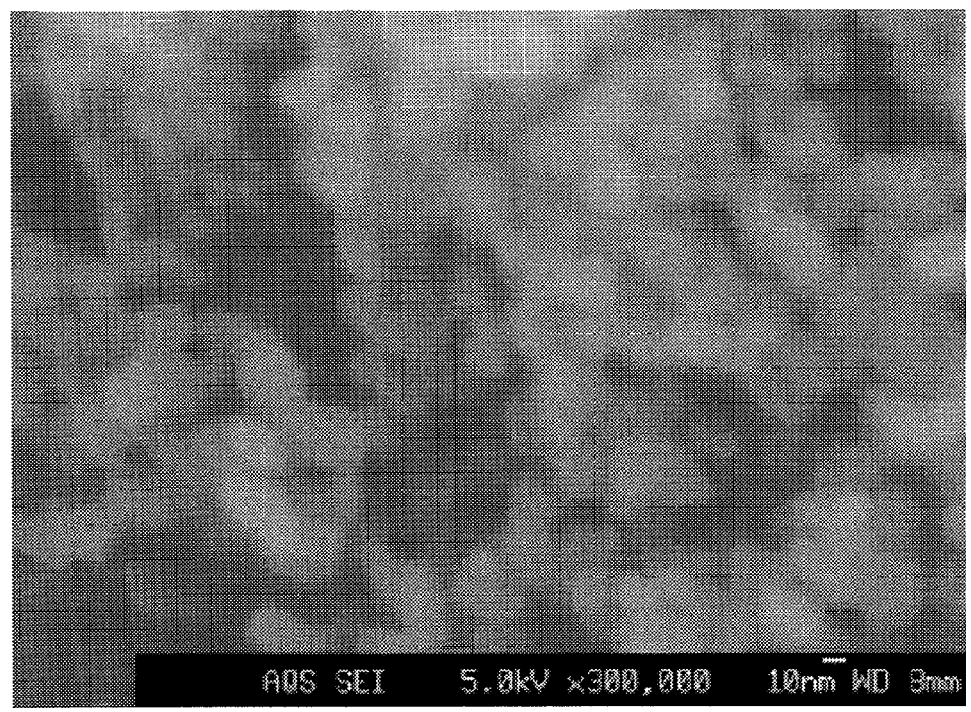
FIGS. 13 and 14 are magnifications of parts of the SEM image of FIG. 12.
Figure 14:
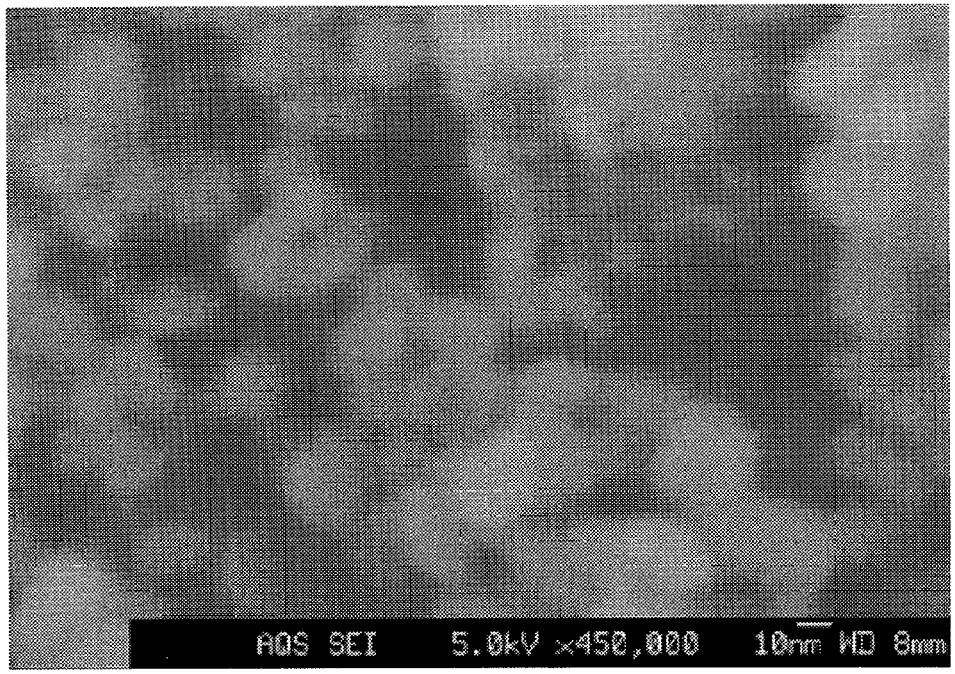

As is seen from FIGS. 12 to 14, the opening size of pores in the surface of the protection layer 140 was at most several tens of nm in Example 2 in the SEM observation. In other words, there were no pores with an opening size greater than or equal to 200 nm (10 times the average particle size D) in the whole surface of the protection layer 140 in Example 2.

Figure 15:
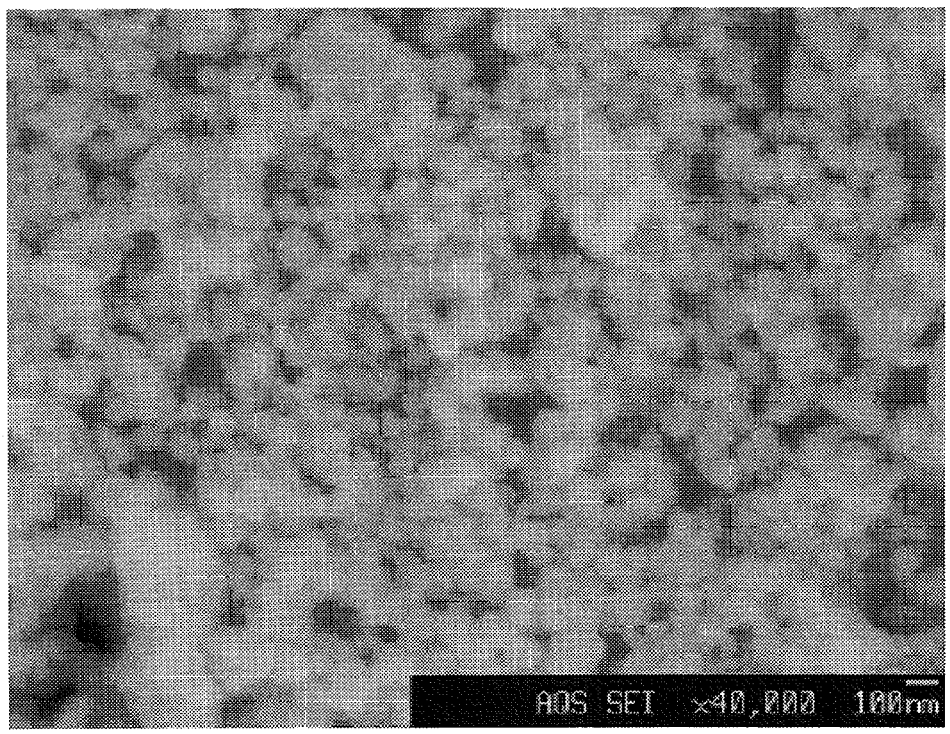
FIG. 15 is a SEM image of protection layer surface in Example 8.

Similarly, the opening size of pores in the surface of the protection layer 140 was at most several hundreds of nm in Example 8 as is seen from FIG. 15. There were no pores with an opening size greater than or equal to 1500 nm (10 times the average particle size D) in the whole surface of the protection layer 140 in Example 8.

Figure 16:
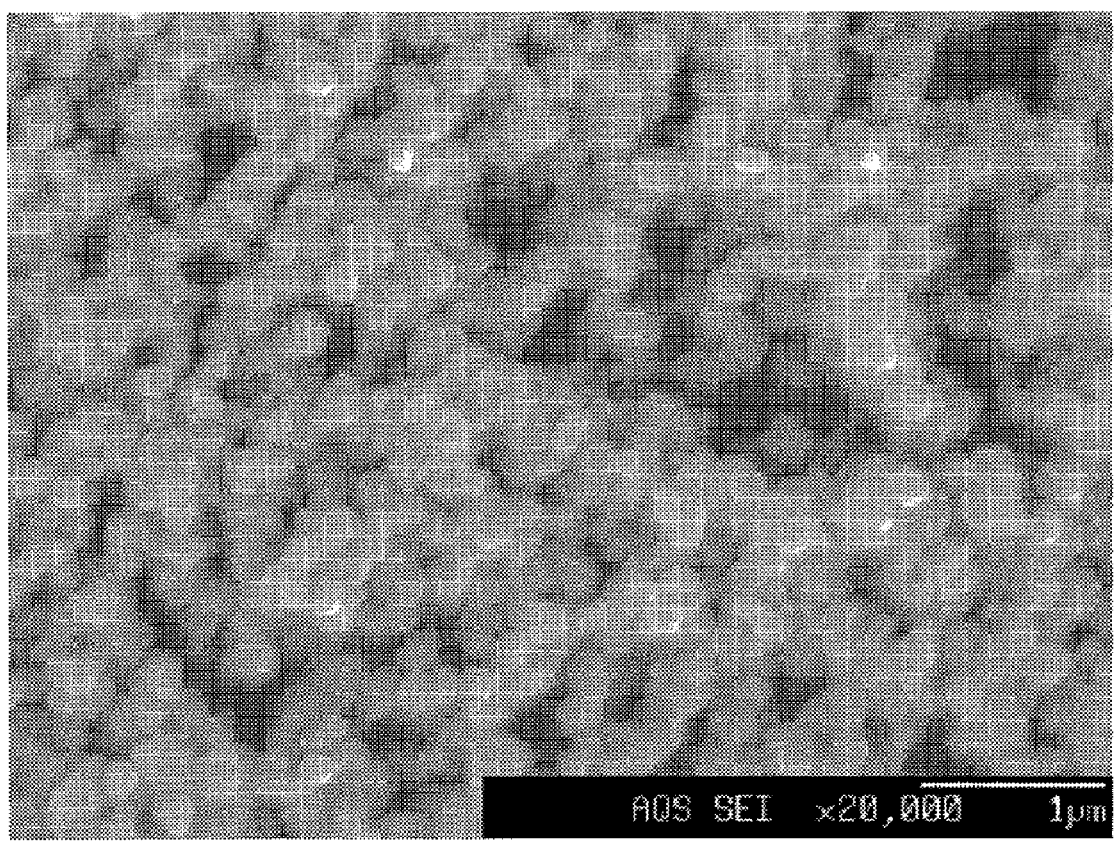
FIG. 16 is a SEM image of protection layer surface in Example 4.

The opening size of pores in the surface of the protection layer 140 was at most several hundreds of nm in Example 4 as is seen from FIG. 16. There were no pores with an opening size greater than or equal to 3000 nm (10 times the average particle size D) in the whole surface of the protection layer 140 in Example 4.

It has also been shown that the gas sensor 100 can attain improved resistance to poisoning by silicon (organic silicon) and prevent secular performance deterioration by the pore size control of the protection layer 140.

The entire contents of Japanese Patent Application No. 2007-007194 (filed on Jan. 16, 2007) and No. 2007-337393 (filed on Dec. 27, 2007) are herein incorporated by reference.

Although the present invention has been described with reference to the above-specific embodiment of the invention, the invention is not limited to this exemplary embodiment. Various modification and variation of the embodiment described above will occur to those skilled in the art in light of the above teachings. The scope of the invention is defined with reference to the following claims.

What is claimed is:

1. A gas sensor, comprising:
    an electrode
    a gas sensing film formed of an oxide semiconductor material and arranged on the electrode so as to cover the electrode by the gas sensing film; and
    a gas-permeable protection layer formed of oxide particles and arranged on and in direct contact with the gas sensing film so as to cover the gas sensing film by the protection layer,
    wherein the oxide particles of the protection layer are unsintered and are closely packed by physical bonding; and
    wherein the oxide particles of the protection layer have an average particle size of 500 nm or smaller.

2. The gas sensor according to claim 1, wherein the protection layer satisfies a relationship of $20 \leq TH/D > 500$, where D is the average particle size (nm) of the oxide particles of the protection layer and TH is the thickness (nm) of the protection layer.

3. The gas sensor according to claim 1, wherein the volume of pores in the protection layer with a pore size smaller than or equal to the average particle size of the oxide particles constitutes 50% or more of the total pore volume of the protection layer.

4. The gas sensor according to claim 1, wherein the volume of pores in the protection layer with a pore size greater than or equal to three times the average particle size of the oxide particles constitutes 10% or less including 0% of the total pore volume of the protection layer.

5. The gas sensor according to claim 1, wherein the volume of pores in the protection layer with a pore size of 200 nm or greater as measured by mercury porosimetry constitutes 5% or less including 0% of the total pore volume of the protection layer.

6. The gas sensor according to claim 1, wherein the protection layer is devoid of pores opening at a surface of the protection layer and having a pore opening size greater than or equal to 10 times the average particle size of the oxide particles.

7. The gas sensor according to claim 1, wherein the oxide particles of the protection layer are formed of titanium oxide.

8. The gas sensor according to claim 1, wherein the gas sensing film is formed of tin oxide.

9. The gas sensor according to claim 1, further comprising: a plurality of catalyst particles scattered over the gas sensing film and covered by the protection layer.

10. The gas sensor according to claim 9, wherein the catalyst particles are unexposed.

* * * * *